United States Patent
Pradeep (10) Patent No.: US 9,962,072 B2
(45) Date of Patent: May 8, 2018

(54) SYSTEM AND METHOD FOR ANALYZING EYE AND CONTACT LENS CONDITION

(71) Applicant: Anantha Pradeep, Piedmont, CA (US)

(72) Inventor: Anantha Pradeep, Piedmont, CA (US)

( * ) Notice: Subject to any disclaimer, the term of this patent is extended or adjusted under 35 U.S.C. 154(b) by 98 days.

(21) Appl. No.: 14/986,538

(22) Filed: Dec. 31, 2015

(65) Prior Publication Data

US 2017/0188805 A1    Jul. 6, 2017

(51) Int. Cl.
*A61B 3/14*    (2006.01)
*A61B 3/00*    (2006.01)
*A61B 5/00*    (2006.01)

(52) U.S. Cl.
CPC .......... *A61B 3/0025* (2013.01); *A61B 5/0022* (2013.01)

(58) Field of Classification Search
CPC ....... A61B 5/0022; A61B 3/0025; A61B 3/14; A61B 3/145; A61B 3/12; G06T 7/0012; G06T 5/003; G06T 5/30; G06T 7/90; H04N 1/628; G06Q 10/10; G06Q 50/22
USPC ........ 351/206, 208, 239, 246; 600/476, 318, 600/558; 382/128; 705/2; 359/894
See application file for complete search history.

(56) References Cited

U.S. PATENT DOCUMENTS

| | | | | |
|---|---|---|---|---|
| 2013/0226008 | A1* | 8/2013 | Dana | A61B 3/14 600/476 |
| 2014/0358011 | A1* | 12/2014 | Jiang | G06T 7/0012 600/476 |

* cited by examiner

*Primary Examiner* — Mustak Choudhury
(74) *Attorney, Agent, or Firm* — Kwan & Olynick LLP (57) ABSTRACT

In general, certain embodiments of the present disclosure provide methods and systems for analyzing eye and contact lens condition. According to various embodiments, a method is provided comprising receiving an image of an eye. The method further comprises extracting condition information of the eye and receiving diagnosis information from a database. The method further comprises comparing the condition information with the diagnosis information and providing an analysis of the eye. In various embodiments, the eye may include a contact lens on the surface of the eye and the condition information may include a condition of the contact lens. In some embodiments, the analysis may include an estimated suggested time to remove the contact lens. In other embodiments, the analysis may include an estimated expiration of the contact lens. In some embodiments, the database may comprise both local storage and global databases access through a global network.

14 Claims, 8 Drawing Sheets

SYSTEM AND METHOD FOR ANALYZING EYE AND CONTACT LENS CONDITION

TECHNICAL FIELD

The present disclosure relates generally to ocular health, and more specifically to automatic diagnosis of eyes and contact lenses.

BACKGROUND

A contact lens is a thin lens placed directly on the surface of the eye. Contact lenses are considered medical devices and can be worn to correct vision, or for cosmetic or therapeutic reasons. People choose to wear contact lenses for many reasons. Aesthetics and cosmetics are often motivating factors for people who would like to avoid wearing glasses or would like to change the appearance of their eyes. Other people wear contacts for functional or optical reasons.

However, many people who wear contact lenses may suffer from contact lens issues, causing a user's eyes to become red, sore, or swollen. There are many different types of contact lenses, from those that are designed to be worn for a few hours, to brands that can safely be worn overnight. Wearing contact lenses for longer than recommended can cause irritation and discomfort. Wearing contact lenses that are worn out or past their use-by date can also cause problems, including infections from bacteria. Contact lens irritation can also cause dry eyes, blurred vision, and a constant feeling of objects in the eye. Such contact lens irritation and discomfort may be caused by improper care or use of contact lenses, wearing contact lenses for too long, or eye infections from contact lenses. Thus, there is a need for an enhanced method for measuring and analyzing the condition of the eye and contact lenses thereon.

SUMMARY

The following presents a simplified summary of the disclosure in order to provide a basic understanding of certain embodiments of the present disclosure. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later.

In general, certain embodiments of the present disclosure provide techniques or mechanisms for measuring the condition of an eye and a contact lens thereon. According to various embodiments, a method is provided comprising receiving an image of an eye. The method further comprises extracting condition information of the eye and receiving diagnosis information from a database. The method further comprises comparing the condition information with the diagnosis information and providing an analysis of the eye.

In yet another embodiment, a system is provided that comprises one or more processors, memory, and one or more programs stored in the memory. In yet another embodiment, a non-transitory computer readable storage medium is provided that stores one or more programs configured for execution by a computer. In various embodiments, the one or more programs may comprise instructions for receiving an image of an eye. The one or more programs may further comprise instructions for extracting condition information of the eye and receiving diagnosis information from a database. The one or more programs may further comprise instructions for comparing the condition information with the diagnosis information and providing an analysis of the eye.

In some embodiments, the condition information may include redness of the eye. In other embodiments, condition information may include moisture of the eye. In other embodiments, condition information may include blood vessel patterns of the eye. In some embodiments, the analysis includes an estimated clinical grade of conjunctival redness. In other embodiments, the eye may include a contact lens on the surface of the eye and the condition information may include a condition of the contact lens. In some embodiments, the analysis may include an estimated suggested time to remove the contact lens. In other embodiments, the analysis may include an estimated expiration of the contact lens. In some embodiments, the database may comprise both local storage and global databases access through a global network.

BRIEF DESCRIPTION OF THE DRAWINGS

The disclosure may best be understood by reference to the following description taken in conjunction with the accompanying drawings, which illustrate particular embodiments of the present disclosure.

DETAILED DESCRIPTION OF PARTICULAR EMBODIMENTS

Reference will now be made in detail to some specific examples of the present disclosure including the best modes contemplated by the inventors for carrying out the present disclosure. Examples of these specific embodiments are illustrated in the accompanying drawings. While the present disclosure is described in conjunction with these specific embodiments, it will be understood that it is not intended to limit the present disclosure to the described embodiments. On the contrary, it is intended to cover alternatives, modifications, and equivalents as may be included within the spirit and scope of the present disclosure as defined by the appended claims.

For example, the techniques of the present disclosure will be described in the context of particular conditions and parts of the eye. However, it should be noted that the techniques of the present disclosure apply to various other parts of the eye. In the following description, numerous specific details are set forth in order to provide a thorough understanding of the present disclosure. Particular example embodiments of the present disclosure may be implemented without some or all of these specific details. In other instances, well known process operations have not been described in detail in order not to unnecessarily obscure the present disclosure.

As used herein, the term "user" shall refer to one implementing the system or method from a user device. As used herein, the term "subject" shall refer to the individual from which the eye being evaluated belongs. Various techniques and mechanisms of the present disclosure will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

OVERVIEW

According to various embodiments, a method for analyzing eye and contact lens condition is provided. The method comprises receiving an image of a subject's eye. In some embodiments, the eye may include a contact lens on the surface of the eye. In some embodiments, the multiple images may be taken of the subject's eye at one or more angles. In some embodiments, dye, such as fluorescein dye may be added to the subject's eye to cause the moisture or various other features to be more visible. According to various embodiments, the method may use an image capturing device to receive the one or more images. In some embodiments, the image capturing device may be any user device, such as a smartphone with a built in camera. In some embodiments, the image capturing device may include a lighting source and/or a lighting detector.

Once the image of a user's eye has been received by the user device, condition information of the eye is extracted from the image. In order to identify certain conditions of the eye, a system may utilize one or more neural networks, computer learning algorithms, and/or other algorithms to automatically detect and identify various objects, colors, and/or patterns in the images. In some embodiments, the condition information may include redness of the eye, moisture of the eye, blood vessel patterns of the eye, or condition of the contact lens itself. In other embodiments, various other condition information may be extracted from the images.

Next, diagnosis information is received from one or more databases. In some embodiments, the databases may be local storage. In other embodiments, the databases may include global databases accessed through a global network, such as the internet. In some embodiments, the diagnosis information may comprise labeled datasets including images labeled with various diagnosis, scores, grades, treatments, etc. The condition information is compared with the received diagnosis. A system may utilize one or more neural networks, computer learning algorithms, and/or other algorithms to automatically identify and retrieve the most relevant diagnosis data. The data of the most relevant diagnosis information may then be compiled to provide an analysis of the eye. In some embodiments, the analysis may include an estimated median clinical grade of conjunctival redness. In other embodiments, the analysis may include an estimated suggested time to remove the contact lens and/or an estimated expiration of the contact lens. In other embodiments, the analysis may include other diagnosis of conditions and/or suggested treatments.

EXAMPLE EMBODIMENTS

Figure 1:
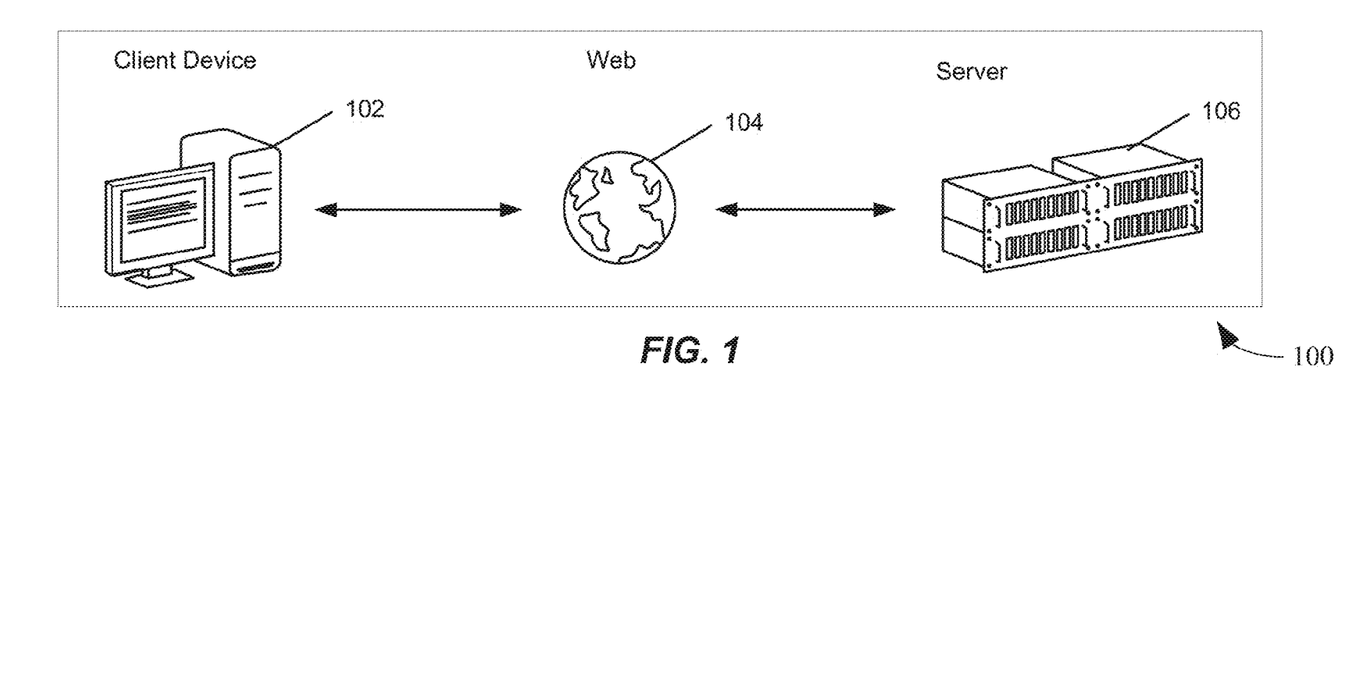
FIG. 1 illustrates a general overview of an example system for implementing various methods of the present disclosure, in accordance with one or more embodiments.

FIG. 1 illustrates a general overview of an example system 100 for implementing various methods of the present disclosure, in accordance with one or more embodiments. In particular, FIG. 1 describes a user accessing the Internet or Web 104 using a computer 102 configured with a web browser to interact with another computer configured as a server 106 containing modules required for fulfilling the user s request.

Figure 2A:
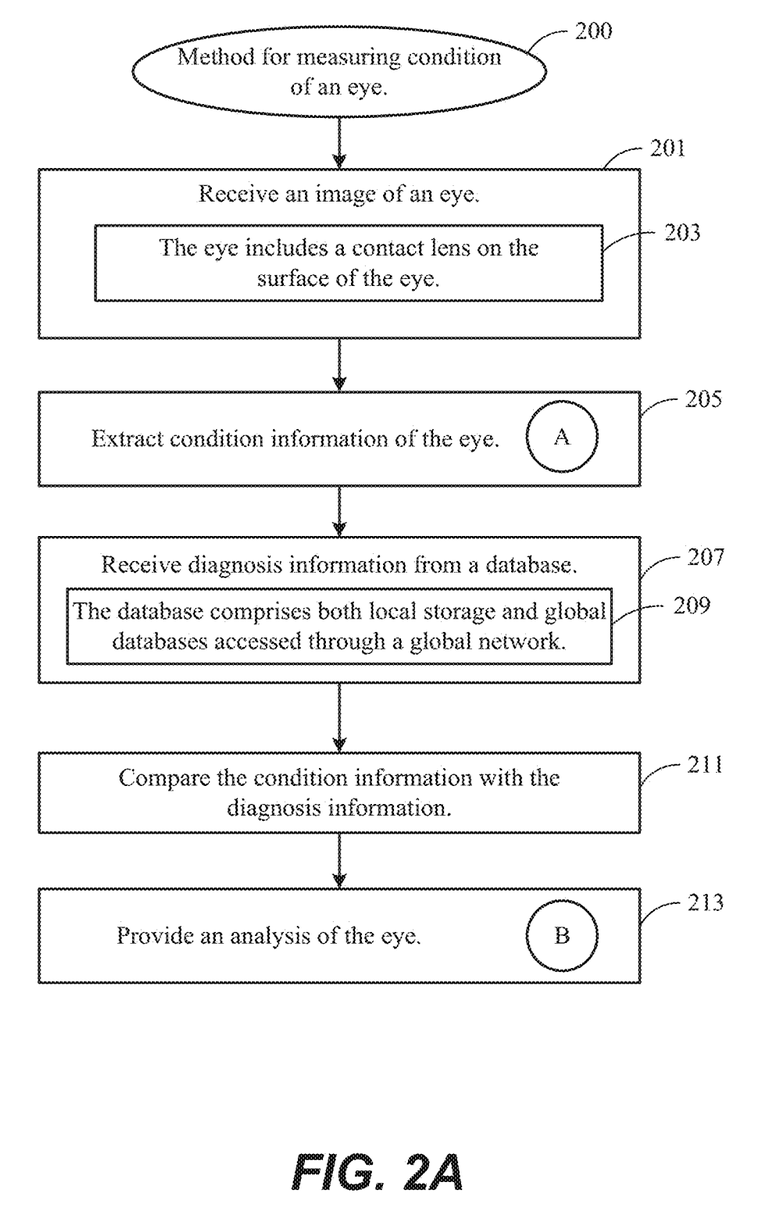
FIGS. 2A-2B illustrate a method for analyzing eye and contact lens condition, in accordance with one or more embodiments.
Figure 2B:
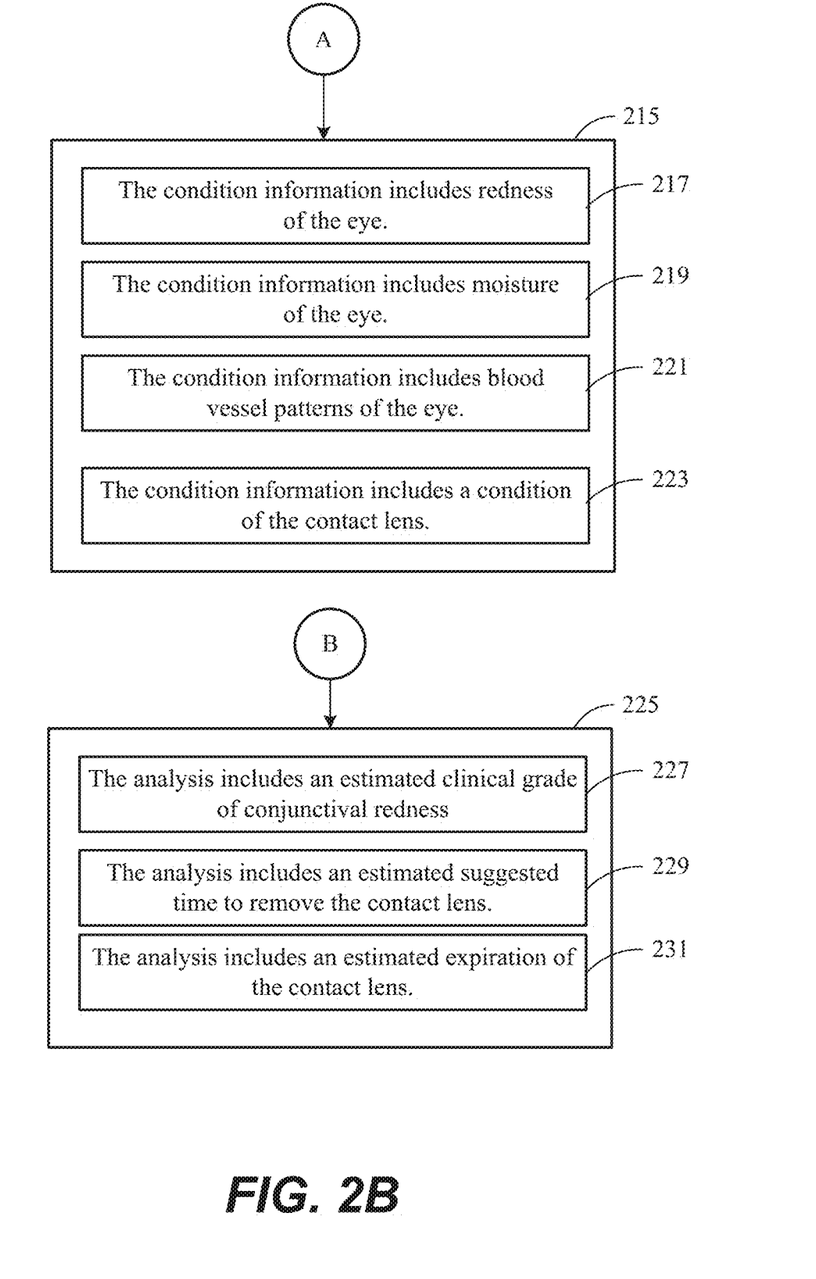

FIG. 2A and FIG. 2B illustrate a method 200 for analyzing eye and contact lens condition, in accordance with one or more embodiments. At step 201, an image of an eye 203 is received. In some embodiments, the eye 203 may include a contact lens on the surface of the eye 203. At step 205 condition information 215 of the eye 203 is extracted. In some embodiments, the condition information 215 may include redness 217 of the eye 203. In other embodiments, the condition information 215 may include moisture 219 of the eye 203. In other embodiments, the condition information 215 may include blood vessel patterns 221 of the eye 203. In other embodiments, the condition information 215 may include a condition 223 of the contact lens.

At step 207, diagnosis information is received from a database 209. In some embodiments, the database 207 may comprise both local storage and global databases accessed through a global network. At step 211, the condition information 215 is compared with the diagnosis information. At step 213, an analysis 225 of the eye 203 is provided. In some embodiments, the analysis 225 may include an estimated clinical grade of conjunctival redness 227. In other embodiments, the analysis 225 may include an estimated suggested time 229 to remove the contact lens. In other embodiments, the analysis 225 may include an estimated expiration 231 of the contact lens.

Figure 3A:
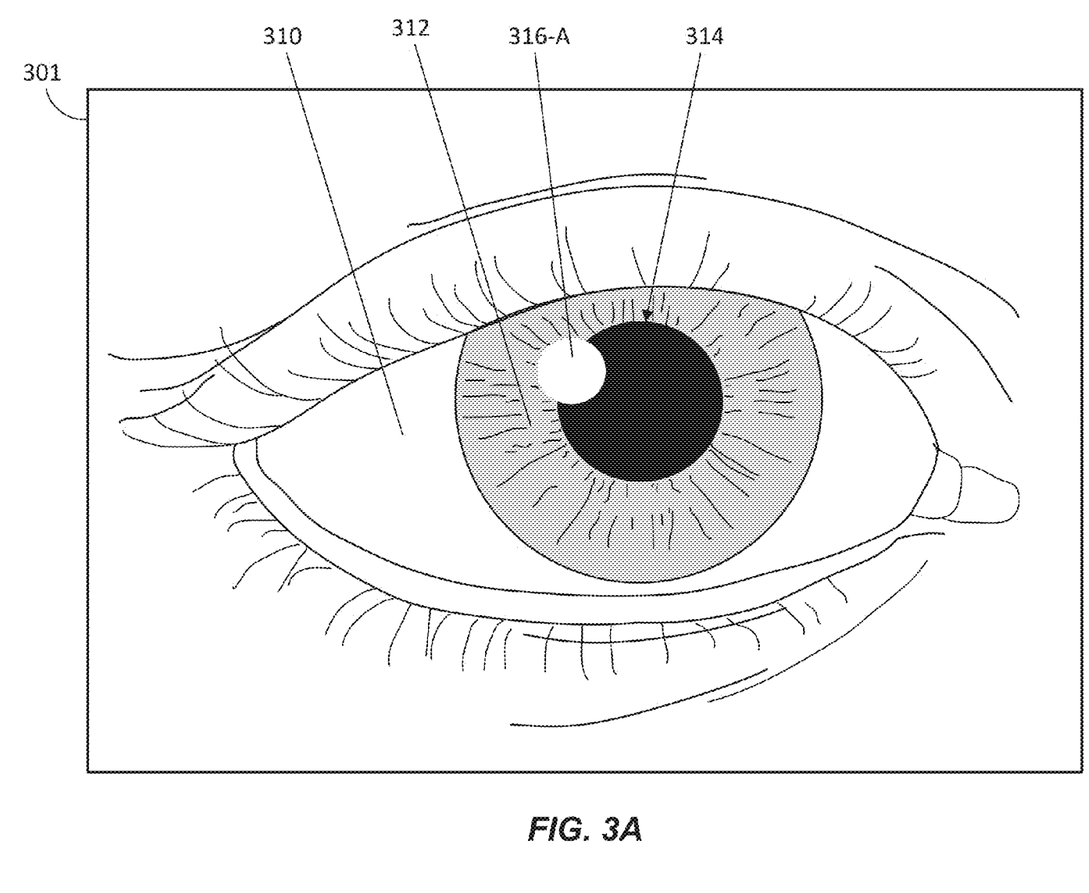
FIG. 3A illustrates an example of an image of an eye, in accordance with one or more embodiments.
Figure 3B:
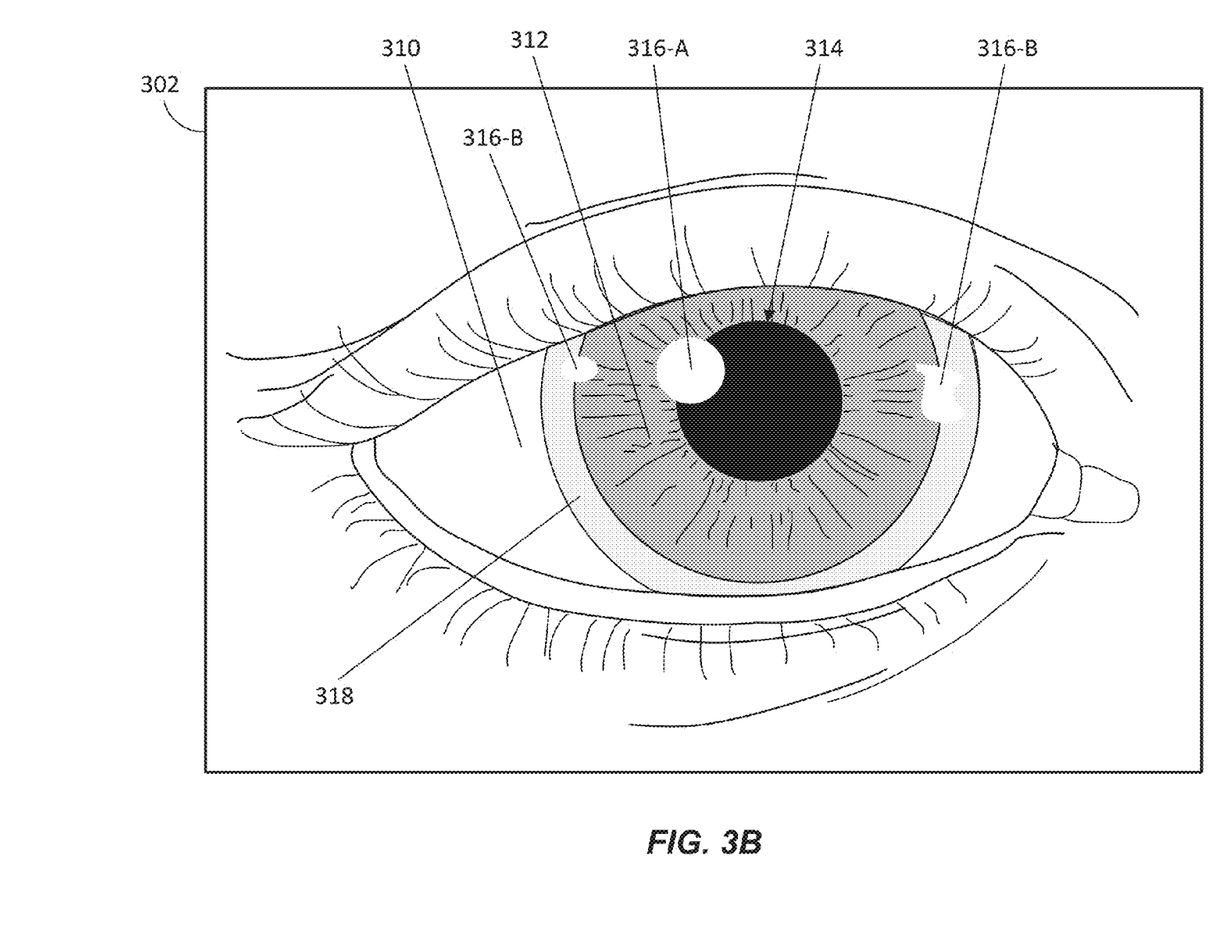
FIG. 3B illustrates an example of an image of an eye with a contact lens on the surface of the eye, in accordance with one or more embodiments.
Figure 3C:
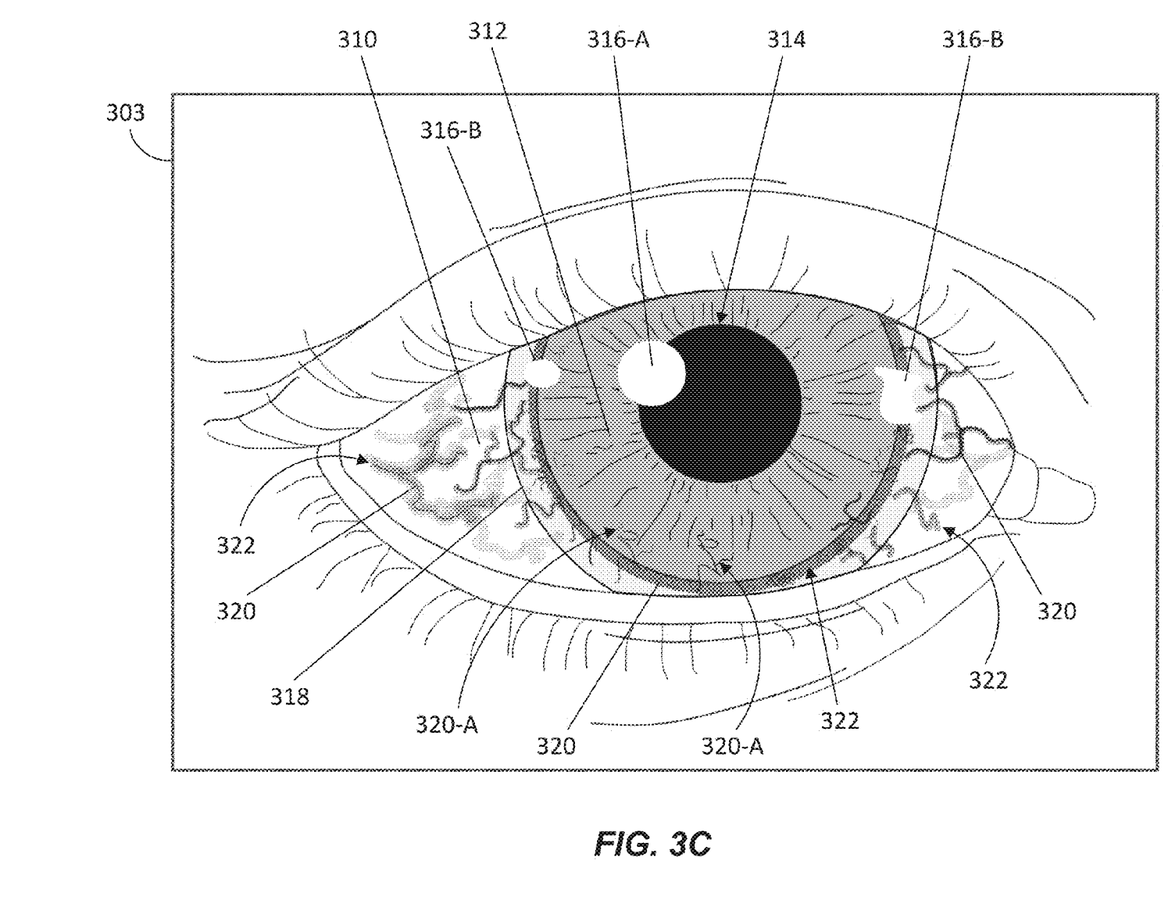
FIG. 3C illustrates an example of an image of an eye including a contact lens on the surface of the eye, blood vessel formation on the eye, and scleral redness on the eye, in accordance with one or more embodiments.

FIG. 3A. FIG. 3B, and FIG. 3C illustrate an examples of images of an eye, in accordance with one or more embodiments. FIG. 3A depicts an image 301 of an eye. FIG. 3B depicts an image 302 of an eye that includes a contact lens on the surface of the eye. FIG. 3C depicts an image 303 of an eye that includes a contact lens on the surface of the eye, blood vessel formation on the eye, and scleral redness on the eye. In some embodiments, images 301, 302, and 303 may be images of a subject's eye 203 received at step 201. In other embodiments, images 301, 302, and 303 may be images stored on a database 207, including local storage or global database.

Images 301, 302, and 303 include sclera 310, iris 312, pupil 314, and reflection 316-A. Image 302 further includes contact lens 318 and contact lens reflections 316-B. Image 303 further includes blood vessels 320 and redness 322. The sclera 310, also known as the white of the eye, is the opaque, fibrous, protective, outer layer of the eye containing collagen and elastic fiber. In humans the whole sclera 310 is usually white, contrasting with the colored iris 312. The iris 312 is a thin, circular structure in the eye, responsible for controlling the diameter and size of the pupil 314 and thus the amount of light reaching the retina. The eye color is defined by the color of the iris 312. In optical terms, the pupil 314 is the eye's aperture and the iris 312 is the diaphragm that serves as the aperture stop. In some embodiments, reflection 316-A may be a reflection caused by a lighting source on a user device or other image capturing device, further described below.

In some embodiments, the image of eye 203 may include a contact lens 318. The contact lens 318 may comprise various types of lenses and materials. For example, in some embodiments, the contact lens 318 may be a corrective contact lens designed to improve vision. In other embodiments, the contact lens 318 may be a cosmetic contact lens. In further embodiments, the contact lens 318 may be a therapeutic scleral lens. In another embodiment, the contact lens 318 may be therapeutic soft lens. In various embodiments, the contact lens 318 may be a rigid lens made from polymethyl methacrylate or a rigid gas permeable material. In various embodiments, the contact lens 318 may be a soft lens made from hydrogel, polymacon, silicone, or other soft lens polymers. In other embodiments, the contact lens 318 may be a hybrid lens with a rigid center and a soft skirt or outer area. In other embodiments, the contact lens 318 may be a daily wear contact lens designed to be worn for one day and removed prior to sleeping or an extended wear contact lens or continuous wear contact lens designed for continuous overnight wear. In some embodiments, contact lens reflection 316-B may be a reflection caused by a lighting source on a user device or other image capturing device, further described below.

In some embodiments, redness 322 of the eye may be caused by formation, injection, and/or prominence of the superficial blood vessels 320 of the conjunctiva, or sclera, which may be caused by disorders of these or adjacent structures. Conjunctivitis and subconjunctival hemorrhage are two of the less serious but more common causes.

Receiving an Image of an Eye

As previously described, an image of an eye 203 is received at step 201. In some embodiments, the image may be an image, such as image 301, 302, or 303. In various embodiments, the image may be received by a user device, such as computer 102 described in FIG. 1. In other embodiments, the image may be received by any other user device, such as a smartphone. In some embodiments such user device receiving the image may utilize one or more neural networks, computer learning algorithms, and/or other algorithms that can analyze and identify various objects, colors, and/or patterns in the image.

In various embodiments, the image may be taken by an image capturing device. In some embodiments, the image capturing device may be a user device, such as a smartphone with a built in camera. In some embodiments, the user device that takes the image may be the same user device that receives the image. In some embodiments, an image capturing device may include commodity off-the-shelf hardware equivalent to that of a modern smartphone. In some embodiments, the image capturing device may include a lighting source. In other embodiments, the image capturing device may include a brightness detector, light meter, or any other means of measuring the level of light at the eye at the time the image is taken. In some embodiments, An example of a user device is further described in FIG. 4.

In some embodiments, multiple images may be taken of the same eye. In some embodiments, the image may be a front view of the eye 203. In other embodiments, the image may be a view of the eye 203 from any one of various angles. As previously described, in some embodiments, the eye 203 may include a contact lens on the surface of eye 203. Examples of a captured image of an eye are depicted in FIGS. 3A, 3B, and 3C.

Extracting Condition Information

Once the image of a user's eye has been received by the user device, condition information 215 of the eye 203 is extracted at step 205. In some embodiments, the system may utilize various neural networks, computer learning algorithms, and/or other algorithms to automatically detect and identify various objects, colors, or patterns, within the image of the eye 203 in order to extract condition information 215. In some embodiments, identification of such objects, colors, and/or patterns may inform what diagnosis information is retrieved in step 207, as further described below.

In various embodiments, the condition information 215 may include redness 217 of the eye 203. In some embodiments, redness 217 may appear as redness 322 or blood vessels 320. Redness of the eye may also be referred to as conjunctivitis and may be caused by infection, allergy, or chemicals. In some embodiments, the image may be scored or categorized based on the concentration of color or amount of color. In some embodiments, the score of redness 217 of the eye 203 may be determined by a predetermined scale. In some embodiments, the predetermined scale may be a simple binary descriptive scale of red and not red. In some embodiments, the score and/or category may correspond to an average concentration of redness within the image. For example, an image, such as image 301, 302, or 303, may be received and input into a neural network as a feature tensor. In some embodiments, the neural network may be trained to separately recognize the sclera 310 of the eye and only measure the coloration in the sclera such that coloration of the iris 312 or pupil 314 are not included. In other embodiments, the eye 203 in an image, such as image 303, may be segmented into two nasal and temporal subsets to allow the two sides of the eye 203 to be analyzed separately.

As previously described, the condition information 215 may include blood vessel patterns 221 of the eye 203. In some embodiments, blood vessel patterns 221 may include blood vessels 320. In some embodiments, the system may recognize various patterns or formations of blood vessels on the eye 203. For example, the system may recognize a subconjunctival hemorrhage, or broken blood vessel, which may be a bright red patch on the sclera of the eye. In some embodiments, a neural network may be trained to identify such red patches. In another example, a neural network may be trained to recognize corneal neovascularization, such as blood vessels 320-A, which may indicate excessive contact lens wear. Corneal neovascularization, depicted as 320-A in FIG. 3C, is abnormal blood vessel growth in the cornea, the clear window on the front of the eye. A normal, healthy cornea has no blood vessel growth. Blood vessels normally circle the cornea at the limbus, the junction of the clear cornea and the sclera 310 of the eye. The limbus is also where the colored iris 312 ends. Any growth beyond this point into the clear cornea may threaten vision. In other embodiments, the diameter and/or size of blood vessels may also be measured.

In other embodiments, the condition information 215 may include moisture 219 of the eye 203. In some embodiments, the moisture of the eye 203 may be indicated by the tear film, the thin layer of tears that cover the exposed area of the globe. In some embodiments, a dye, such as fluorescein dye, may be added to the subject's eye 203 to cause the moisture of the tears in the eye 203 to be more visible. In other embodiments, the image capturing device may include a lighting source that is secured at a fixed position relative to the subject's eye 203. In some embodiments, the lighting source may create one or more reflections 316-A on the eye 203 and/or reflections 316-B on a contact lens located on the eye 203. In some embodiments, one or more reflections, 316-A and/or 316-B created by the lighting source may be located in the same position among various images of the eye 203 because the lighting source is at a fixed position relative to the subject's eye 203. In some embodiments, the amount of reflection in reflections 316-A and/or 316-B may be measured and the image may be assigned a reflectivity score. In some embodiments, the reflectivity score may be correlated to the moisture level of the eye 203 and/or the contact lens. As additionally described, the image capturing device may include a brightness detector, light meter, or any other means of measuring the level of light at the eye at the time the image is taken. In some embodiments, such light measurements may additionally refine the calculation of the reflectivity score. In other embodiments, the lighting of the image may be adjusted such that the image may be accurately compared to other images at step 211. In some embodiments, a neural network may recognize the one or more reflections and measure the reflectivity of the reflections and assign a reflectivity score.

In other embodiments, the image capturing device may detect and identify various qualities of the eye's tear film. The tear film of an eye is composed of three separate layers, and a deficiency in any one of the three layers will result in an inadequate tear film. The mucin layer lies closest to the eye and is produced by the cells on the eye's surface. These cells can be damaged by exposure to certain chemicals and medications, heat, or autoimmune disorders. The aqueous (watery) layer is produced by the lacrimal glands. Function of the lacrimal glands can diminish with age or certain diseases. The lipid layer is also known as the oily layer. The eyelids have a special row of oil glands called meibomian glands that open onto the surface of the eye. With each blink, the oils secreted from these glands coat the surface of the watery layer, preventing the watery layer from evaporating too quickly between blinks. In some embodiments, multiple images may be taken of eye 203 without any blinking by the subject in between. In some embodiments, a dye, such as fluorescein dye, may be added to the surface of eye 203 to cause the moisture to be more visible. The difference in reflections 316-A and/or 316-B between the images may be measured to determine an amount of evaporation of moisture.

In other embodiments, the condition information 215 may include a condition 223 of the contact lens, such as contact lens 318. In some embodiments, the system may utilize various neural networks, computer learning algorithms, and/or other algorithms to automatically detect and identify a contact lens 318 in the image and differentiate the contact lens 318 from the subject's eye 203. In other embodiments, various neural networks, computer learning algorithms, and/or other algorithms may also be used to identify the condition 223 of the contact lens 318.

In some embodiments, a condition 223 of the contact lens 318 may include cloudiness of the contact lens 318. In various embodiments, cloudiness of a contact lens 318 may be caused by protein deposit buildup, dry-eye syndrome, dry lenses, or contact lens deterioration and scratching. A common cause of contact lens blurriness is the buildup of protein on the surface of the lens. Eyes are naturally designed to self-clean through tear production. While normally this works to provide clear comfortable vision, contacts may disrupt this cleaning process. Protein and other oils that are found in your tears have a tendency to attach themselves to the microscopic grooves found in most contact lenses, and any outside contaminants that would normally get cleared away also have a chance to attach to the contact lens as well. After an extended period of time, this accumulates a film over the top of the lens, resulting in distorted, blurry, and cloudy vision.

In some embodiments, lens cloudiness may also result from deterioration of the contact lens itself. This is usually caused by external scratching, overuse of the contact lens, or using corrosion by chemicals. Additional to protein and particle buildup, foggy contacts may result from inflamed and dried-out eyes, which is typically associated with dry-eye syndrome. Dry eye syndrome not only can cause cloudy vision, but can also result in an increased susceptibility to infection and damage. Dry eye symptoms can be especially bad in people who wear soft contact lenses. Soft lenses absorb water from the eye surface and make the eye dry. Dryness may lead to patchy loss of cells in the cornea.

In some embodiments, cloudiness is detected and/or measured by determining the opaqueness or clarity of the contact lens 318. In some embodiments, a contact lens 318 may cover the subject's eye 203 including the iris 312, pupil 314, and part of the sclera 310. In such embodiments, the cloudiness of the contact lens 318 may be determined by comparing the part of the sclera 310 not covered by the contact lens 318 with the part of the sclera 310 that is covered by the contact lens 318. In some embodiments, the moisture level of the contact lens 318 may be extracted as described above. In other embodiments, scratches and/or corrosion of the contacts may be measured. In some embodiments, a dye, such as fluorescein dye or other appropriate dye, may be added onto the subject's eye to cause certain features that may be present in the eye 203 or contact lens 318 to be more visible, such as surface texture, scratches, corrosion, or moisture. For example, fluorescein dye may be used on the surface of the eye 203 to show small areas of staining that may indicate punctate epithelial erosions, which may be a sign of contact lens overuse.

In further embodiments, extracting condition information 215 at step 205 may further include prompting a user to input one or more sensations, including pain level, type of pain sensation (stinging, burning, itching, irritation, etc.), other discomfort, abnormal feeling of something in the eye (foreign body, scratched area), excessive watering (tearing) of the eyes, unusual eye secretions, redness of the eyes, reduced sharpness of vision (poor visual acuity), blurred vision, rainbows, or halos around objects, sensitivity to light (photophobia), dry eyes, etc. In other embodiments, extracting condition information 215 at step 205 may further include prompting a user to input one or more characteristics of the contact lens 318, including, but not limited to: contact lens type, material, brand, date of first use, etc. In further embodiments, extracting condition information 215 may include prompting a user to input identification information of the subject, including name, age, gender, etc.

Receiving Diagnosis Information

Diagnosis information is received at step 207 from a database 209. According to various embodiments, the diagnosis information may comprise a labeled dataset including a collection of images of various eyes. In some embodiments, the images in the labeled dataset may be images, such as images 301, 302, and/or 303. In some embodiments, each image in the collection of images may be labeled with information pertaining to a diagnosed condition for the eye in that image. For example, images in a labeled dataset may include information about one or more of the following: redness level, blood vessel size, blood vessel pattern, color of iris, color of cornea, color of sclera, etc. The images in a labeled dataset may also include information about contact lenses in the images, including: clarity, type, deterioration level, etc. In some embodiments, the labeled dataset may additionally include diagnosed conditions for each image. In some embodiments, the diagnosed conditions may be made by professional clinicians and/or other medical professionals.

For example, in some embodiments, the images may be a collection of images labeled with a predetermined level of redness, or redness score. In some embodiments, the level of redness may be previously determined by a neural network, computer learning algorithm, and/or other algorithm. In other embodiments, the level of redness in the images may be previously graded by one or more medical professional. In some embodiments, the level of redness may be an average or other value determined by another form of mathematical computation of all grades given to the image.

As previously described, the database 207 may comprise both local storage and global databases accessed through a global network, in various embodiments. In some embodiments, local storage may be located in computer 102 or other client device. In some embodiments, the global databases may be one or more servers 106 as described in FIG. 1. In some embodiments, the global databases may be accessed through a global network such as internet 104. In some embodiments, all images and/or diagnosis information in one or more databases 209 may be received. In some embodiments, images form one or more databases 209 are received by a user device, such as computer 102.

In some embodiments, diagnosis information may be automatically received based on the condition information 215 extracted in step 205. For example, if redness, such as redness 322, is detected, images related to scleral redness may be retrieved from one or more databases 209. In some embodiments, a score is given to the level of redness, images, such as 301, 302, or 303, of eyes with the same and/or similar redness. In such embodiments, scores may be retrieved from one or more databases 209. In another example, if a particular blood vessel pattern, such as a hemorrhage or corneal neovascularization 320-A, is detected, images with similar blood vessel patterns may be retrieved from one or more databases 209.

In other embodiments, diagnosis information may be automatically received based on identification information of the subject. As previously described, extracting condition information 215 at step 205 may include prompting a user to input various identification information of the subject. In some embodiments, such identification information includes medical record information. In some embodiments, the databases 209 may include stored images of the subject's eye in various conditions. In some embodiments, the stored images may include images of a subject's eye at a baseline state. For example, the stored images may include images of a subject's eye in a healthy state. In other embodiments, the stored images may include images of a subject's eye with a certain amount of redness or blood vessel pattern. In some embodiments, the stored images may include images of a subject's eye without contact lenses. In other embodiments, the stored images may include images of a subject's eye with a contact lens in new and/or undamaged condition. In some embodiments, the stored images may be labeled with diagnosis information, including date, diagnosis, pain, contact lens type, material, brand, date of first use, etc. In other embodiments, diagnosis information may be received at step 207 by prompting a user for input of information corresponding to the subject or the subject's eye 203, including the information and images described in this paragraph.

Comparing Condition Information and Diagnosis Information

The extracted condition information 215 is compared with the received diagnosis information at step 211. In some embodiments, the condition information 215 may be compared to the diagnosis information by determining the diagnosis information that most closely corresponds to the condition information 215. In some embodiments, the diagnosis information, such as stored images are given a similarity score based on similarity to the image of the subject's eye. For example, a stored image may be image 301 and the image of the subject's eye may be image 303. In various embodiments, the system may utilize a neural network, computer learning algorithm, and/or other algorithm to automatically compare and score the stored images 301. In some embodiments, diagnosis information corresponding to stored images 301 that meet a predetermined threshold similarity score are extrapolated to be provided at step 213.

For example, a particular pattern of corneal neovascularization 320-A may be extracted from the image 303 of the subject's eye 203 at step 205. Stored images that include corneal neovascularization may be received from one or more databases at step 207. Then at step 211, the stored images are compared with the image 303 of the subject's eye 203 and scored and ranked based on similarity, degree of vascularization, degree of redness 322, etc.

In other embodiments, images stored in one or more databases may be labeled with same and/or related condition information 215 input by the user. In some embodiments, such stored images with the same and/or related condition information are retrieved and may be compared to the image 303 of the subject's eye 203. In some embodiments, stored images that most closely match the image 303 of the subject's eye 203 are identified. In further embodiments, the diagnosis information associated with the identified matching images is extrapolated to be provided in step 213.

For example, at step 205, a user may input that the subject feels a sharp pain along with sending an image, such as image 303. Stored images may be retrieved that are labeled with sharp pain. The stored images may then be compared to image 303 to be scored and ranked based on similarity. As another example, diagnosis information in one or more databases may be retrieved based on identification information of the subject based on user input. Some of the diagnosis information may include previously stored images of the subject's eye with a new, undamaged contact lens, such as image 302. This previously stored image 302 may be compared to the image 303 of the subject's eye 203 to determine any change in clarity and/or cloudiness of the contact lens 318. As another example, diagnosis information in one or more databases 209 may include a previously stored image 301 of the subject's eye without a contact lens 318. Such previously stored images 301 may be compared to the image 303 of the subject's eye 203 to determine whether a contact lens 318 is in the image 303 of the subject's eye 203.

Providing Analysis of the Eye

At step 213, an analysis 225 of the eye 203 is automatically provided. In various embodiments, analysis 225 may include a diagnosis of the eye 203 in an image, such as image 303. In some embodiments, the analysis 225 may include an estimated clinical grade of conjunctival redness 227. As previously described, in some embodiments, received diagnosis information may include images labeled with a predetermined level of redness, or some other redness score previously determined by one or more medical professionals. In some embodiments, the redness score may be an average or other value determined based on all scores previously given. In some embodiments, such value may be included in analysis 225. In other embodiments, one or more images in the diagnosis information may be determined to have the same level of redness as image 303 of the subject's eye 203, but may include differing diagnosed redness levels. In such embodiments, the system may provide an average of the scores as analysis 225.

Similarly, other scores and/or grades may be provided for other detectable factors. In some embodiments, analysis 225 may include a diagnosis of blood vessel formation. In some embodiments, analysis 225 may include a diagnosis of abnormal blood vessel growth patterns and/or formations, including subconjunctival hemorrhages, corneal neovascularization (320-A), etc. In some embodiments, the diagnosis may be created by comparison of an eye 203 in an image, such as 303, with images in the received diagnosis information at step 207. In other embodiments, moisture level of eye 203 and/or contact lens 318 in an image, such as 303, may be estimated in analysis 225 by comparing image 303 with the images in the received diagnosis information at step 207. In some embodiments, analysis 225 may include a diagnosis of the condition of one or more layers of the tear film of eye 203. In other embodiments, analysis 225 may include the degree of cloudiness or opaqueness of a contact lens 318. In some embodiments, scores for each of the factors are normalized and then added together. In such embodiments, if the total sum of the normalized factor scores reach a predetermined threshold (or do not reach a predetermined threshold for reverse scales), then an analysis of good-bad will be given. In some embodiments, the scores for each factor are input into one or more equations for determining the condition of the eye or contact lens. In such embodiments, the output of the one or more equations determines whether it is time to take out the contact lens and/or replace the lens with a new lens.

In other embodiments, the analysis 225 may include an estimated suggested time 229 to remove the contact lens 318. For example, the analysis can provide that the current contact lens, with the current condition of the eye, has a wearable shelf-life of 12 more hours before needing to be replaced. In some embodiments, such a diagnosis may utilize calculated information regarding redness 322, formation and size of blood vessels 320, or moisture of eye 203 or contact lens 318. In some embodiments, such a diagnosis may also utilize information input by the user, including start time of contact lens use, lens type, brand, etc. For example, given a certain level of redness determined by the system and a user input of the number of hours already worn, the system may provide an analysis 225 that recommends that the contact lens 318 may be worn for a maximum of two more hours. In some embodiments, analysis 225 may include a diagnosis of contact lens overuse. In some embodiments, an estimated suggested time 229 may include a number of recovery hours and/or days before a subject may resume wearing contact lenses. For example, the system may detect and identify a blood vessel pattern 221 of cornea neovascularization, such as 320-A in image 303. By comparing this condition information 215 to relevant diagnosis information, the system may provide an analysis of the severity of the vascularization of the cornea, a description of the symptoms and causes, as well as a suggested recovery time before reusing contact lenses. In other embodiments, analysis 225 may include a recommendation to clean a contact lens 318 to remove protein build-up.

In other embodiments, the analysis 225 may include an estimated expiration 231 of the contact lens 318. In some embodiments, analysis 225 may include a determination of a remaining duration before the contact lens 318 needs to be replaced. In some embodiments, such estimated expiration may be based on the identification of contact lens cloudiness resulting from scratching, corrosion, or other deterioration of the contact lens itself. For example, external scratching or corrosion from harsh chemicals may be detected, identified, and quantified in steps 205, 207, and 211. In other embodiments, such diagnosis may also utilize information input by the user, including start date of contact lens use, lens type, brand, etc.

In other embodiments, analysis 225 may include multiple possible diagnosis for an image, such as image 303. In some embodiments, analysis 225 may include probabilities corresponding to the likelihood that each given diagnosis is correct. In further embodiments, the analysis 225 may include a description of symptoms, causes, and other facts about each given diagnosis. In various embodiments, analysis 225 may further include suggested treatments for each given diagnosis, including visiting a medical professional. In various embodiments, analysis 225 may include suggested products, including lubrication drops, medication, ointments, lotions, or other medications. For example, the system may extract condition information 215 corresponding to moisture and compare such condition information 215 with relevant diagnosis information to determine dryness of the eye 203. The analysis 225 may include various diagnosis of deficiencies in the mucin layer, watery layer, and/or oily layer. The analysis 225 may provide probabilities that each diagnosis is correct. The analysis 225 may provide suggested treatments, such as eye drops or steroids for the mucin layer, plugging the puncta on the subject's eyelids for the water layer, or a warm compress for thickened or blocked oil.

Figure 4:
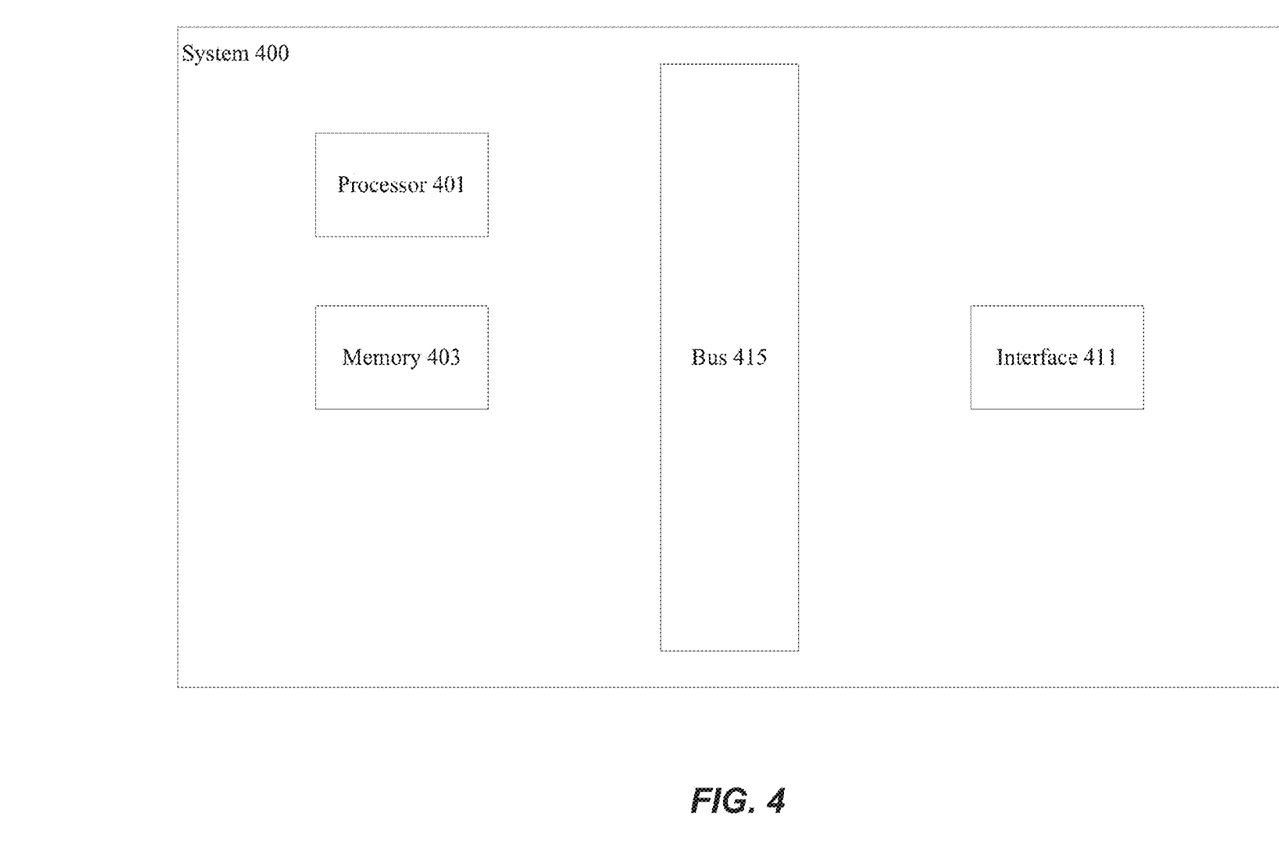
FIG. 4 illustrates one example of a system for extracting condition information of an eye, in accordance with one or more embodiments.

FIG. 4 illustrates one example of a system 400 for extracting condition information of an eye, in accordance with one or more embodiments. In some embodiments, system 400 may be a client device, such as client device 102. In other embodiments, system 400 may be a server device, such as server 106. According to particular embodiments, a system 400, suitable for implementing particular embodiments of the present disclosure, includes a processor 401, a memory 403, an interface 411, and a bus 415 (e.g., a PCI bus or other interconnection fabric) and operates as a streaming server. In some embodiments, when acting under the control of appropriate software or firmware, the processor 401 is responsible for processing inputs through various computational layers and algorithms to extract condition information from images and other data. In other embodiments, the processor 401 is responsible for receiving diagnosis information from one or more databases and comparing the diagnosis information to the extracted condition information. Various specially configured devices can also be used in place of a processor 401 or in addition to processor 401. In other embodiments, system 400 may also include one or more of the following: an image capturing device, an image processor, a lighting source, and a lighting detector.

The interface 411 is typically configured to send and receive data packets or data segments over a network, such as network 104. Particular examples of interfaces supports include Ethernet interfaces, frame relay interfaces, cable interfaces, DSL interfaces, token ring interfaces, and the like. In addition, various very high-speed interfaces may be provided such as fast Ethernet interfaces, Gigabit Ethernet interfaces. ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the system 400 uses memory 403 to store data and program instructions for operations including extracting condition information from images and other data, such as in step 205, receiving diagnosis information form one or more databases, such as in step 207, and comparing condition and diagnosis information to provide an analysis of the image, such as in steps 211 and 213 respectively. The program instructions may control the operation of an operating system and/or one or more applications, for example. The memory or memories may also be configured to store received metadata and batch requested metadata.

Because such information and program instructions may be employed to implement the systems/methods described herein, the present disclosure relates to tangible, or non-transitory, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

Figure 5:
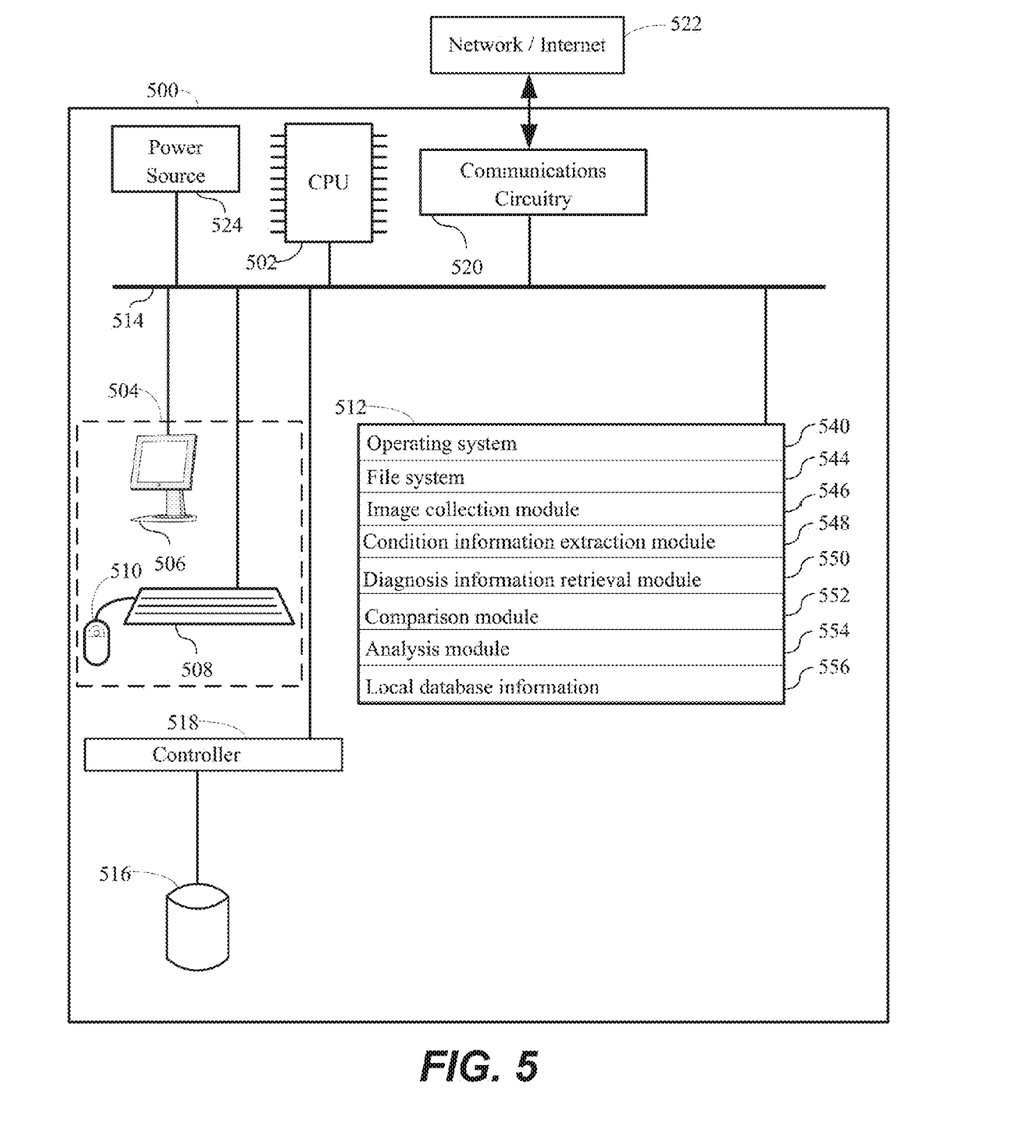
FIG. 5 is a block diagram illustrating an example of a computer system capable of implementing various processes described in the present disclosure.

FIG. 5 is a block diagram illustrating an example of a computer system capable of implementing various processes described in the present disclosure. The system 500 typically includes a power source 524; one or more processing units (CPU's) 502 for executing modules, programs and/or instructions stored in memory 512 and thereby performing processing operations; one or more network or other communications circuitry or interfaces 520 for communicating with a network 522; controller 518; and one or more communication buses 514 for interconnecting these components. In some embodiments, network 522 can be the another communication bus, the Internet, an Ethernet, an Intranet, other wide area networks, local area networks, and metropolitan area networks. Communication buses 514 optionally include circuitry (sometimes called a chipset) that interconnects and controls communications between system components. System 500 optionally includes a user interface 504 comprising a display device 506, a keyboard 508, and a mouse 510. Memory 512 includes high-speed random access memory, such as DRAM, SRAM. DDR RAM or other random access solid state memory devices; and may include non-volatile memory, such as one or more magnetic disk storage devices, optical disk storage devices, flash memory devices, or other non-volatile solid state storage devices. Memory 512 may optionally include one or more storage devices 516 remotely located from the CPU(s) 502. Memory 512, or alternately the non-volatile memory device(s) within memory 512, comprises a non-transitory computer readable storage medium. In some embodiments, memory 512, or the computer readable storage medium of memory 512 stores the following programs, modules and data structures, or a subset thereof:

an operating system 540 that includes procedures for handling various basic system services and for performing hardware dependent tasks;

a file system 544 for storing various program files;

an image collection module 546 for receiving images, such as images 301, 302, or 303 of an eye 203.

a condition information extraction module 548 for taking an image input and identifying particular objects, colors, and/or patterns, as well as prompting a user for input at user interface 504;

a diagnosis information retrieval module 550 for receiving data and images by searching various local storage 516 and/or global databases on network 522, or prompting user for input at user interface 504;

a comparison module 552 for comparing and matching input data with data received from various local storage 516 and/or global databases on network 522 and/or from prompted user input;

an analysis module 554 for providing one or more possible diagnosis, probabilities for each diagnosis, degree of conditions, and/or suggest treatments and medications based on the results produced by comparison module 552; and local database information 556 comprising condition information, diagnosis information and other subject information.

Each of the above identified elements may be stored in one or more of the previously mentioned memory devices, and corresponds to a set of instructions for performing a function described above. One or more of the above identified modules my operate by retrieving input from one or more local storage 516 or global databases on network 522, prompting for user input at user interface 504, or providing a user with a template at user interface 504. The above identified modules or programs (i.e., sets of instructions) need not be implemented as separate software programs, procedures or modules, and thus various subsets of these modules may be combined or otherwise re-arranged in various embodiments. In some embodiments, memory 512 may store a subset of the modules and data structures identified above. Furthermore, memory 512 may store additional modules and data structures not described above.

Although FIG. 5 shows a "system for analyzing eye and contact lens condition," FIG. 5 is intended more as functional description of the various features which may be present in a set of servers than as a structural schematic of the embodiments described herein. In practice, and as recognized by those of ordinary skill in the art, items shown separately could be combined and some items could be separated. For example, some items shown separately in FIG. 5 could be implemented on single servers and single items could be implemented by one or more servers. The actual number of servers used to implement a presentation generation system and how features are allocated among them will vary from one implementation to another, and may depend in part on the amount of data traffic that the system must handle during peak usage periods as well as during average usage periods.

While the present disclosure has been particularly shown and described with reference to specific embodiments thereof, it will be understood by those skilled in the art that changes in the form and details of the disclosed embodiments may be made without departing from the spirit or scope of the present disclosure. It is therefore intended that the present disclosure be interpreted to include all variations and equivalents that fall within the true spirit and scope of the present disclosure. Although many of the components and processes are described above in the singular for convenience, it will be appreciated by one of skill in the art that multiple components and repeated processes can also be used to practice the techniques of the present disclosure.

What is claimed is:

1. A method for analyzing eye and contact lens condition comprising:
   receiving an image of an eye, having a contact lens on the eye surface;
   assigning a reflectivity score to the image;
   scoring the image using concentration of color and amount of color using a predetermined scale;
   extracting condition information of the eye and of the contact lens condition;
   receiving diagnosis information from a database;
   comparing the condition information with the diagnosis information; and
   providing an analysis of the eye, including an estimated suggested time to remove the contact lens and an estimated expiration of the contact lens, wherein a neural network accepts the image and recognizes a specific part of the eye such that only that specific part is measured for coloration.

2. The method of claim 1, wherein condition information includes redness of the eye.

3. The method of claim 1, wherein condition information includes moisture of the eye.

4. The method of claim 1, wherein the condition information includes blood vessel patterns of the eye.

5. The method of claim 1, wherein the analysis includes an estimated clinical grade of conjunctival redness.

6. The method of claim 1, wherein the database comprises both local storage and global databases accessed through a global network.

7. A system for analyzing eye and contact lens condition comprising:
   one or more processors;
   memory;
   one or more programs stored in the memory, the one or more programs comprising instructions for:
      receiving an image of an eye having a contact lens on the eye surface;
      assigning a reflectivity score to the image;
      scoring the image using concentration of color and amount of color using a predetermined scale;
      extracting condition information of the eye and of the contact lens condition;
      receiving diagnosis information from a database;
      comparing the condition information with the diagnosis information; and
      providing an analysis of the eye including an estimated suggested time to remove the contact lens and an estimated expiration of the contact lens, wherein a neural network accepts the image and recognizes a specific part of the eye such that only that specific part is measured for coloration.

8. The system of claim 7, wherein condition information includes redness of the eye.

9. The system of claim 7, wherein condition information includes moisture of the eye.

10. The system of claim 7, wherein the information includes blood vessel patterns of the eye.

11. The system of claim 7, wherein the analysis includes an estimated clinical grade of conjunctival redness.

12. The system of claim 7, wherein the database comprises both local storage and global databases accessed through a global network.

13. A non-transitory computer readable storage medium storing one or more programs configured for execution by a computer for analyzing eye and contact lens condition, the one or more programs comprising instructions for:
   receiving an image of an eye having a contact lens on the eye surface;
   assigning a reflectivity score to the image;
   scoring the image using concentration of color and amount of color using a predetermined scale;
   extracting condition information of the eye and of the contact lens condition;
   receiving diagnosis information from a database;
   comparing the condition information with the diagnosis information; and
   providing an analysis of the eye including an estimated suggested time to remove the contact lens and an estimated expiration of the contact lens, wherein a neural network accepts the image and recognizes a specific part of the eye such that only that specific part is measured for coloration.

14. The non-transitory computer readable storage medium of claim 13, wherein the database comprises both local storage and global databases accessed through a global network.

* * * * *